United States Patent [19]

Komatsu et al.

[11] 4,263,452
[45] Apr. 21, 1981

[54] PROCESS FOR PURIFYING TEREPHTHALIC ACID

[75] Inventors: Makoto Komatsu; Ryoichi Oda, both of Kurashiki, Japan

[73] Assignee: Mitsubishi Gas Chemical Company, Inc., Tokyo, Japan

[21] Appl. No.: 147,283

[22] Filed: May 6, 1980

Related U.S. Application Data

[63] Continuation-in-part of Ser. No. 48,445, Jun. 14, 1979, abandoned.

[30] Foreign Application Priority Data

Jun. 12, 1979 [GB] United Kingdom ............ 7920472/79
Jun. 19, 1979 [DE] Fed. Rep. of Germany ....... 2924665
Jun. 20, 1979 [NL] Netherlands .......................... 7904840
Jun. 21, 1979 [FR] France .................................. 7915964

[51] Int. Cl.$^3$ ............................................. C07C 51/42
[52] U.S. Cl. .................................... 562/487; 562/416; 562/486
[58] Field of Search ..................... 562/487, 416, 486

[56] References Cited

FOREIGN PATENT DOCUMENTS 1085929 10/1967 United Kingdom ..................... 562/487

OTHER PUBLICATIONS

T 880,007, Paris et al., 11/24/70.

Primary Examiner—Alan Siegel
Attorney, Agent, or Firm—Armstrong, Nikaido, Marmelstein & Kubovcik

[57] ABSTRACT

Crude terephthalic acid obtained by oxidation of p-tolualdehyde in a liquid phase with molecular oxygen in the presence of a bromine compound as a catalyst, using water as a solvent is purified by dissolving the crude terephthalic acid in water, hydrogenating the aqueous solution of terephthalic acid with molecular hydrogen in the presence of a hydrogenating catalyst, and recrystallizing the terephthalic acid from the hydrogenated aqueous solution, where an alkaline material such as a hydroxide, a carbonate, or a bicarbonate of sodium, potassium, calcium or barium is added to the aqueous solution of terephthalic acid to be purified before the hydrogenation.

The purified terephthalic acid has a very low 4-CBA content, and no hydrogenation catalyst activity is lowered by the addition of the alkaline material.

6 Claims, No Drawings

PROCESS FOR PURIFYING TEREPHTHALIC ACID

This Application is a continuation-in-part application of Application Ser. No. 48445, filed on June 14, 1979 now abandoned.

This invention relates to a process for purifying terephtalic acid obtained by oxidation of p-tolualdehyde in a liquid phase in the presence of a bromine compound as a catalyst, using water as a solvent.

Reaction of oxidizing p-xylene in the presence of heavy metal salts of cobalt, manganese, etc. and a bromine compound as catalysts, using a lower aliphatic monocarboxylic acid as a solvent to obtain terephthalic acid is disclosed in Japanese Patent Publication No. 2666/59, and is widely utilized in an industrial scale.

Reaction of oxidizing an aromatic compound containing an alkyl substituent or a partially oxidized alkyl substituent in a water solvent in the presence of a bromine ion to obtain terephthalic acid is also known from Japanese Patent Publication No. 1392/64: British Patent specificaton No. 833,438.

Furthermore, production of terephthalic acid by oxidation of p-toluic acid in a water solvent containing hydrogen bromide is disclosed in Japanese Laid-open Patent Application No. 4019/71: U.S. Pat. No. 3,678,106.

However, the terephthalic acid produced according to any of these prior art processes usually contains 4-carboxybenzaldehyde, which will be hereinafter referred to as 4-CBA, a reaction intermediate, or colored or coloring materials of unknown structures, and is colored yellow. Thus, the terephthalic acid, as it is, cannot be directly used for reaction with glycols to form polyesters, and must be further purified to obtain terephthalic acid of direct polymerization grade.

On the other hand, processes for producing terephthalic acid with a high purity by purifying crude terephthalic acid containing impurities are known from Japanese Patent Publications Nos. 16860/66 and 33189/74, where terephthalic acid is dissolved in water as a recrystallization solvent; a hydrogenation reaction or a decarbonylation reaction is carried out in the presence of a catalyst at the dissolution in water to convert the reaction intermediate or coloring materials to the material readily purificable; and terephthalic acid is recrystallized to obtain terephthalic acid with a high purity.

The present inventors made studies of purification of terephthalic acid obtained by the water solvent process according to the art disclosed in said Japanese Patent Publication No. 16860/66, and found that the purification of terephthalic acid obtained by the water solvent process was more difficult than that of terephthalic acid obtained by an acetic acid solvent process.

As a result of extensive studies to solve the problem, the present inventors found that the terephthalic acid obtained by the water solvent process contained a very small amount of bromine compounds, whereas the terephthalic acid obtained by the acetic acid solvent process contained no analyzable amount of the bromine compounds at all. As a result of further studies of behavior of the bromine compounds in the hydrogenation reaction, the present inventors found that the bromine compounds were converted to hydrogen bromide by an action of hydrogen. That is, it was found that, when the crude terephthalic acid formed in the acetic acid solvent was dissolved in water and hydrogenated at an elevated temperature according to the procedure disclosed in said Japanese Patent Publication No. 16860/66, a mother liquid resulting from the recrystallization of terephthalic acid contained no analyzable amount of hydrogen bromide, whereas when the crude terephthalic acid formed in the water solvent and hydrogenated in the same manner as above, a mother liquor resulting from the recrystallization of terephthalic acid contained a very small amount of hydrogen bromide.

Presuming that the hydrogen bromide lowers a hydrogenation catalyst activity, the present inventors added sodium hydroxide containing at least one equivalent weight of sodium to the bromine atoms contained in the crude terephthalic acid to the aqueous solution of terephthalic acid to be purified in advance, and then conducted hydrogenation and recrystallization, and found that no lowering of the hydrogenation catalyst activity was observed.

The present invention is based on such a finding a provides a process for purifying crude terephthalic acid obtained by oxidizing p-tolualdehyde in a liquid phase with molecular oxygen in the presence of a bromine compound as a catalyst, using water as a solvent by dissolving the crude terephthalic acid in water and hydrogenating the resulting aqueous solution with molecular hydrogen in the presence of a hydrogenating catalyst, and recrystallizing terephthalic acid from the solution, which comprises adding an alkaline material to the terephthalic acid before the hydrogenation.

The amount of the alkaline material to be added can be at least one equivalent weight to the bromine atoms contained in the crude terephthalic acid to be purified. Even if the amount of the alkaline material to be added is in excess of the equivalent weight to the bromine atoms, the catalytic activity itself is not adversely influenced thereby, or rather a preferable result can be sometimes obtained thereby, because it seems that a very small amount of polymeric impurities can be prevented from accumulation in pores of activated carbon as a hydrogenation catalyst carrier, but a true reason has not been clarified yet. Of course, it is not preferable to increase the amount of the alakaline material to such a degree as to lower the purification efficiency of terephthalic acid. Therefore, the amount of the alkaline material to be added to 100 parts by weight of the crude terephthalic acid is less than 2.5 parts by weight, preferably less than 1 part by weight.

The alkaline material used in the present invention includes hydroxides, carbonates, bicarbonates, etc. of sodium, potassium, calcium, barium, etc.

The catalyst used in the oxidation of p-tolualdehyde in the present invention is a bromine compound capable of generating bromine ions under reaction conditions such as hydrogen bromide, ethyl bromide, sodium bromide plus hydrogen chloride, etc., and heavy metals such as cobalt, manganese, etc. are not always required.

The amount of the bromine compound to be added is 0.8–10% by weight as bromine atoms on the basis of water as the solvent. When the amount of bromine compound is less than 0.8% by weight, the starting material p-tolualdehyde undergoes vigorous combustion reaction, lowering the terephthalic acid yield. When the amount of the bromine compound is too large on the other hand, the oxidation reaction proceeds rapidly, and purely white terephthalic acid cannot be obtained, and by-products such as 4-CBA are increased, lowering the yield of the desired terephthalic acid. The preferable amount of the bromine compound for the most preferable yield of terephthalic acid is 2-7% by weight as the bromine atoms on the basis of water as the solvent.

Oxidation reaction temperature is in a range of 180°-250° C., preferably 200°-240° C. When the oxidation reaction temperature is too low, the oxidation reaction does not proceed sufficiently, whereas when the reaction temperature is too high, the combustion reaction takes place rapidly, and purely white terephthalic acid cannot be obtained.

Oxidation reaction pressure generally automatically depends upon step of keeping the reaction temperature constant by evaporation of water solvent and condensing and refluxing operation, but it is possible to keep the reaction pressure to a desired constant value by an outside heat-exchanger means. The pressure range is not particularly restricted, so long as the reaction solution can be kept in a liquid phase, but usually is 10–70 kg/cm² gage.

An oxidizing agent is either oxygen or air, but it is economically advantageous to use air.

The solvent used in the oxidation reaction is water, and it is necessary to add water as the solvent to the reaction system in an amount of at least 1.5 times as much as the starting material p-tolualdehyde by weight.

The terephthalic acid resulting from the oxidation reaction is crude terephthalic acid containing 0.01–1.0% by weight, particularly 0.05–0.3% by weight, of 4-CBA, and after being separated from the water solvent, the crude terephthalic acid is redissolved in water and hydrogenated in the presence of a hydrogenating catalyst. Various hydrogenating catalysts can be used for that purpose, and for example, noble metal elements of Group VIII of the periodic table, such as ruthenium, rhodium, palladium, osmium, iridium, platinum, etc., and iron, cobalt, nickel, etc. supported on a carrier such as activated carbon, diatomaceous earth, etc. can be used in a very fine powder form, or in a salt or in a form of Raney nickel or platinum or palladium black.

Hydrogenation temperature must be a temperature at least convenient for complete dissolution of terephthalic acid, and is usually 200°-330° C., preferably 225°-300° C.

Hydrogenation pressure is not particularly restricted, so long as the aqueous solution can be kept in a liquid phase, and is usually 16–100 kg/cm² gage.

Hydrogenation time depends upon a desired purity of purified terephthalic acid and contact condition with hydrogen, and is usually 0.005-10 hours, preferably 0.01-2 hours.

In carrying out the present invention, p-tolualdehyde is continuously supplied into a water solvent containing 0.8–10% by weight of bromine ions as bromine atoms or into a reactor together with the water solvent, and continuously oxidized with molecular oxygen under such oxidation reaction conditions as:

| Reaction temperature: | 180°-240° C. |
|---|---|
| p-tolualdehyde feed rate (LSV): | 0.1-0.35 kg/hr . l (based on the solvent) |

The resulting terephthalic acid is separated from the reaction solution, and is redissolved in water to completely dissolve the precipitated crude terephthalic acid. Then, an alkaline material is added to the aqueous solution of terephthalic acid, and the aqueous solution of terephthalic acid is brought in contact with hydrogen in the presence of a hydrogenating catalyst at a temperature of 200°-330° C. for a contact time of 0.005-10 hours. The hydrogenated aqueous solution is cooled, and the precipitated pure terephthalic acid is separated from the solution, and the mother liquor is recycled to the oxidation reaction for reuse as a solvent.

In the oxidation reaction, water is used as a solvent, but terephthalic acid with a high purity can be readily produced by hydrogenation in the present invention, where a lowering of hydrogenating catalyst activity can be effectively prevented at the same time.

EXAMPLE 1 p-tolualdehyde was continuously fed to an autoclave (net capacity: 2 l) filled with 900 g of water solvent containing 3% by weight of hydrogen bromine at a rate of 300 g/hr at 230° C. for one hour, and oxidation was carried out semi-continuously. After cooling, the resulting terephthalic acid was taken out of the autoclave, washed with water at the normal temperature, and dried.

Properties of terephthalic acid are as follows:

| 4-CBA | 3,030 ppm |
|---|---|
| $OD_{340}$ | 1.23 |

$OD_{340}$ represents an absorbance at 340 m$\mu$ obtained by measurement by placing a solution of 2 g of terephthalic acid in 25 ml of 2N-KOH in a 50 mm cell.

The resulting terephthalic acid contained 2,100 ppm of bromine compounds as bromine atoms.

300 g of the resulting crude terephthalic acid (containing 0.63 g of bromine atoms, i.e. $7.9 \times 10^{-3}$ gram-equivalents of bromine atoms), 0.35 g of sodium hydroxide (containing $8.75 \times 10^{-3}$ gram-equivalents of sodium atoms), and 900 g of water were filled in an autoclave (net capacity: 2 l) with a stirrer.

Then, the autoclave was filled with hydrogen to 15 kg/cm² gage, and heated to 280° C. When the autoclave reached that temperature, a case filled with 27 g of a Pd-activated carbon catalyst whose initial acitivity had been developed by a hydrogenation reaction in advance and whose activity was made steady, was dipped in the terephthalic acid solution in the autoclave by an outside signal, and the state of 280° C. was kept for one hour. After the completion of the hydrogenation reaction, the autoclave was slowly cooled to precipitate terephthalic acid.

Quality of the resulting purified terephthalic acid is given below:

| 4-CBA | 10 ppm |
|---|---|
| $OD_{340}$ | 0.088 |

EXAMPLES 2 and 3

Purification of crude terephthalic acid obtained in the same oxidation conditions as in Example 1 was carried out in the same manner as in Example 1 except that the amount of the alkali to be added was changed. The results are shown below

| | Ex. 2 | Ex. 3 |
|---|---|---|
| Amount of NaOH added | 0.9 g | 3.0 g |

-continued

|  | Ex. 2 | Ex. 3 |
|---|---|---|
| Quality of purified terephthalic acid | | |
| 4-CBA | 10 ppm | 15 ppm |
| $OD_{340}$ | 0.080 | 0.090 |
| Terephthalic acid recovery | 99% | 98% |

Comparative Example 1

The crude terephthalic acid obtained under the same oxidation conditions as in Example 1 was purified in the same manner as in Example 1 except that no sodium hydroxide was added.

Quality of the resulting purified terephthalic acid is as follows:

| 4-CBA | 35 ppm |
|---|---|
| $OD_{340}$ | 0.119 |

Comparative Example 2

Purification of crude terephthalic acid obtained under the same oxidation conditions as in Example 1 was carried out in the same manner as in Example 1, except that an amount of the alkali over the range of the present invention was added thereto. The results are given below

| Amount of NaOH added | |
|---|---|
| 10.5 g | |
| Quality of purified terephthalic acid | |
| 4-CBA | 30 ppm |
| $OD_{340}$ | 0.120 |
| Terephthalic acid recovery | |
| 92% | |

When the amount of the alkaline material exceeds the range of the present invention, the quality of the resulting purified terephthalic acid is deteriorated, and the terephthalic acid recovery is lowered.

Reference Example

Crude terephthalic acid produced from p-xylene as a starting material, using acetic acid as a solvent and cobalt, manganese and bromine as a catalyst in an industrial scale was purified in the same manner as in Example 1.

Quality of the crude terephthalic acid is as follows:

| 4-CBA | 1,320 ppm |
|---|---|
| $OD_{340}$ | 0.670 |

Quality of purified terephthalic acid is as follows:

| 4-CBA | 3.5 ppm |
|---|---|
| $OD_{340}$ | 0.045 |

When the purification of terephthalic acid obtained by the oxidation using water as a solvent was carried out without adding an alkaline material thereto, it was observed that the catalyst activity was lowered, but the lowering of catalyst activity could be prevented by adding the alkaline material thereto.

What is claimed is:

1. In a process for purifying crude terephthalic acid obtained by oxidation of p-tolualdehyde in a liquid phase with molecular oxygen in the presence of a bromine compound as a catalyst, wherein said crude terephthalic acid is dissolved in water, the resulting aqueous solution of terephthalic acid is hydrogenated with molecular hydrogen in the presence of a hydrogenating catalyst, and the terephthalic acid is recovered from the hydrogenated aqueous solution, the improvement comprising: (a) adding less than 2.5 parts by weight of an alkaline material to the aqueous solution of terephthalic acid before the hydrogenation per 100 parts by weight of the crude terephthalic acid; and (b) recrystallizing the terephthalic acid from the hydrogenated solution by cooling said solution without prior acidification.

2. A process according to claim 1, wherein the alkaline material is a hydroxide, a carbonate, or a bicarbonate of sodium, potassium, calcium or barium.

3. A process according to claim 1, wherein at least an equivalent weight of the alkaline material to bromine atoms contained in the crude terephthalic acid is added to the aqueous solution of terephthalic acid.

4. In a process for purifying a crude terephthalic acid containing a bromine compound which forms hydrogen bromine on hydrogenation wherein said crude terephthalic acid is dissolved in water, the resulting aqueous solution of terephthalic acid is hydrogenated with molecular hydrogen in the presence of a hydrogenating catalyst, and the terephthalic acid is recovered from the hydrogenated aqueous solution, the improvement comprising: (a) adding to the aqueous terephthalic acid solution before hydrogenating it less than 2.5 parts by weight of an alkaline material per 100 parts by weight of the crude terephalic acid and (b) recrystallizing the terephthalic acid from the hydrogenated solution without prior acidification by cooling said solution to a temperature effective for causing the terephthalic acid to separate therefrom.

5. A process according to claim 4 wherein the alkaline material is a hydroxide, a carbonate or a bicarbonate of sodium, potassium, calcium or barium.

6. A process according to claim 4 wherein at least an equivalent weight of the alkaline material to bromine atoms contained in the crude terephthalic acid is added to the aqueous solution of terephthalic acid.

* * * * *